United States Patent [19]

Marlar et al.

[11] Patent Number: 5,093,263

[45] Date of Patent: Mar. 3, 1992

[54] METHOD OF MAKING AND USING A PLEDGET COMPOSITION TO MINIMIZE INTERFERENCES IN MEASURING CALCIUM ION CONCENTRATION OF BLOOD

[75] Inventors: Richard A. Marlar, Englewood; David C. Kressin, Lakewood; Michael D. Iliff, Conifer, all of Colo.

[73] Assignee: Marquest Medical Products, Inc., Englewood, Colo.

[21] Appl. No.: 594,655

[22] Filed: Oct. 9, 1990

[51] Int. Cl.$^5$ .................. G01N 1/00; G01N 31/00; G01N 33/20; A61B 5/00

[52] U.S. Cl. .................. 436/18; 422/102; 128/760; 604/226; 436/79; 436/174

[58] Field of Search .............. 422/102; 436/74, 18, 436/63, 79, 150; 604/226; 435/2; 536/21; 73/864.21-864.28; 128/760, 763

[56] References Cited

U.S. PATENT DOCUMENTS

| | | | |
|---|---|---|---|
| 3,941,565 | 3/1976 | Schwarz | 436/74 |
| 4,371,516 | 1/1983 | Gregory et al. | 424/22 |
| 4,479,799 | 10/1984 | Thiel | 604/187 |
| 4,501,719 | 2/1985 | Williams | 422/102 |
| 4,521,975 | 6/1985 | Bailey | 34/5 |
| 4,687,000 | 8/1987 | Eisenhardt et al. | 128/760 |

OTHER PUBLICATIONS

"Facilitated Determination of Ionized Calcium," by Urban et al., Clinical Chemistry, vol. 31, No. 2, pp. 264-266 (1985).

"Heparinization of Samples for Plasma Ionized Calcium Measurement," by Heining et al., Critical Care Medicine, vol. 16, No. 1, pp. 67-68 (1988).

Primary Examiner—David L. Lacey
Assistant Examiner—Thomas E. Daley
Attorney, Agent, or Firm—Sheridan Ross & McIntosh

[57] ABSTRACT

A pledget containing an anticoagulant for use with a blood sample is provided. The pledget includes a filler material, such as dextran, to increase the volume anticoagulant to minimize interference with free ion measurements in the blood.

8 Claims, 3 Drawing Sheets

METHOD OF MAKING AND USING A PLEDGET COMPOSITION TO MINIMIZE INTERFERENCES IN MEASURING CALCIUM ION CONCENTRATION OF BLOOD

FIELD OF THE INVENTION

The present invention relates to pledgets that are useful as anticoagulating agents in blood, blood plasma and the like, a process for producing such pledgets, and a method of utilizing the pledgets. More particularly, the present invention relates to pledgets containing heparin and a glucose polymer filler.

BACKGROUND OF THE INVENTION

Whole blood or blood plasma is collected from human beings for a variety of reasons. These can include analytical reasons such as analysis of the blood for foreign matter, or can be for reasons such as the collection and distribution to hospitals for use during, for example, surgical operations.

One of the problems associated with collecting blood, is that when blood leaves the body, it has a tendency to coagulate. Because of this, it is common to collect the blood into a receptacle that contains an anticoagulant. This anticoagulant will typically prevent or inhibit the reaction that clots (coagulates) blood. Examples of anticoagulants include trypsin inhibitor, hirudin, and heparin, heparin being the most common anticoagulant for blood. As used herein, the term blood refers to blood in its various forms, including whole blood or blood plasma.

Heparin is a mucopolysaccharide composed of sulfated D-glucosamine and D-glucuronic acid. Heparin is a heterogenous compound and it is estimated that the molecular weight can vary from about 6,000 to about 20,000. The primary anticoagulation function of heparin is believed to be the prevention of the formation of thrombin in the blood clotting process.

Heparin is commercially available in a wide range of activity concentrations, usually expressed in U.S.P. units per milligram, or units/mg. For example, the activity concentration of heparin can range from about 140 units/mg to about 250 units/mg.

Traditionally, a concentration of from about 50 to about 400 U.S.P. units of heparin activity per milliliter of blood (units/ml) is used to anticoagulate a blood sample. As used herein, the term "unit" is used to refer to the United States Pharmacopoeia (U.S.P.) unit of heparin activity. Another common measurement of activity is the international unit, or IU. The international unit is believed to be about 6.4 percent larger then the U.S.P. unit.

The present inventors believe that one of the many reasons that high concentrations (i.e. 50 units/ml of blood and higher) of heparin have been utilized in blood sampling receptacles, is that there is a surface effect, particularly with glass, that promotes the coagulation of blood. Therefore, it was desirable to use high concentrations of heparin in glass blood sampling receptacles to inhibit the coagulation of the blood. Further, the use of heparin did not substantially bias any subsequent analyses, so there was little motivation to seek a reduction in the concentration.

Today, blood is often drawn from a patient into a plastic receptacle for blood gas analysis. Additionally, advances in blood analyzing technology have enabled medical personnel to measure the free ion concentration in the blood, including free calcium ions. For example, devices for measuring free calcium in blood are available from Nova Biomedical Corporation, Waltham, Mass., ABX Corporation, Horsham, Pa., and Ciba-Corning, Severna Park, Md.

The need to accurately measure free calcium ion in a patient's blood is important in a number of instances. For example, medical personnel require accurate free calcium ion measurements for patients with hypertension to predict which patients will benefit from an increase in the oral intake of calcium. Free calcium ion is also routinely measured when a major medical decision may be influenced by the patient's calcium status, for example, decisions relating to endocrine disorders. Further, sick newborn children are susceptible to losing calcium easily and may not readily reabsorb it, so accurate measurements are required.

However, heparin compounds are known to chelate free calcium ions, and therefore bias the measurement of free calcium ions. As a result, when traditional concentrations of heparin are used for anticoagulation in a collected blood sample, the free calcium ion measurement can be significantly biased.

Numerous techniques have been suggested to overcome this particular problem. U.S. Pat. No. 4,687,000 by Eisenhardt et al., issued Aug. 18, 1987, discloses a method for treating blood with an anticoagulant, preferably heparin, and compensating for the anticoagulant binding of several cation species by adding compensating amounts of the cations to the blood sample. The concentration of the cation species thus remains constant in the blood sample and may be determined by subsequent analysis. However this procedure necessitates the determination of the extent that cation species are bound, requiring experimentation and theoretical assumption.

Another approach to solving the chelation problem is to lower the concentration of heparin in the blood sample so that the chelating effects on the free ions are minimized.

For example, in "Facilitated Determination of Ionized Calcium," by Urban et al., *Clinical Chemistry*, Vol. 31, No. 2, pp. 264–266 (1985), such a method for determining the amount of ionized calcium in blood is disclosed. In the experiment, sodium heparin was utilized in a concentration of between about 10 and about 25 IU/ml of whole blood and a calcium heparin preparation in a concentration of about 20 IU/ml of whole blood was also utilized It is disclosed that the use of sodium heparin in a concentration less than 5 IU/ml yielded free ionized calcium measurements similar to those obtained for a reference serum. However, there was frequent clogging of the electrode system, indicating poor anticoagulation action. Further, it is disclosed that the proper heparin dilution was difficult to prepare.

In "Heparinization of Samples for Plasma Ionized Calcium Measurement," by Heining et al., in *Critical Care Medicine*, Vol. 16, No. 1, pp. 67–68 (1988), it is disclosed that when heparin is used in concentrations greater than about 10 IU/ml of blood, complexes form with the calcium ions. It is concluded that for measurement of plasma-free ionized calcium, blood samples should be heparinized in a quantified fashion to insure that the heparin concentration does not exceed 10 IU/ml of whole blood. If the concentration exceeds this level, it is alleged that falsely low readings will be obtained. However, such low concentrations of heparin are difficult to control, particularly outside of the research laboratory. For instance, a three cubic centimeter (3 cm$^3$) syringe may have from 0.5 to 3.0 cubic centimeters of blood drawn into it when used in practical situations. Deviations in the amount of heparin activity in the blood sampling device may result in a significant increase in the concentration of heparin activity in the blood sample and lead to a biasing of free ion measurements.

Hence, due to the biasing effect on the measurement of ions, it is preferable to use a very low unit dosage of heparin as an anticoagulant to minimize the biasing effect. The heparin may be introduced into the blood in many forms, including as a solid pledget or as a liquid. Solid pledgets are preferred since excess liquid heparin can result in over-dilution of the blood sample and accentuated binding of ions, such as calcium, to the heparin. However, the production of solid pledgets containing low unit dosages has been found to be extremely difficult to implement.

A pledget is a single unit dosage of heparin in tablet form. A process for the manufacture of a pledget is described, for example, in commonly-owned U.S. Pat. No. 4,521,975 by Bailey, issued June 11, 1985. This patent describes a process for the production of a pledget wherein the predetermined unit dosage is formed by a lyophilizing process.

However, the pledgets produced by the process disclosed by Bailey are used to anticoagulate blood samples such that the heparin concentration is from about 100 to about 200 units/ml of blood. Recent advances in blood-analyzing technology have dictated that much lower levels of heparin be used.

If the pledget is made purely of heparin, and the heparin has an average activity of about 180 units/mg of heparin, a pledget providing 2.8 U.S.P. units of heparin would have a mass of about 16 micrograms, a volume of approximately 11 microliters, yielding a density of only about 1.5 mg/ml. Such a small size with such low density is very difficult to manufacture, particularly on a commercial scale. It would be advantageous to manufacture larger pledgets, which are more easily handled by existing machinery.

One possible solution is to place the heparin compound on a carrier body. U.S. Pat. No. 4,687,000 by Eisenhardt, et al., discussed hereinabove, describes carrier bodies used with heparin compositions. It is disclosed that the carrier body may, for example, be made of material such as filter paper, synthetic fibers, glass fibers, mineral fibers, or the like. For example, filter paper is used to absorb the heparin solution and create a carrier body with the desired level of heparin. However, one of the problems with using these materials is that it is very difficult to control the concentration of heparin in any individual dose. Further, the disclosed materials do not substantially dissolve and may interfere with the proper operation of the blood sampling or analyzing device.

U.S. Pat. No. 4,479,799 by Thiel, issued on Oct. 30, 1984, discloses that one method for introducing an anticoagulant such as heparin into a blood sample is to place an anticoagulant tablet in the hub of the needle of the syringe used to obtain the blood sample from the patient. It is disclosed that the tablets may comprise a heparin salt, a tablet binder and a pH controlling substance. It is disclosed that the use of these tablets requires a mixing step after the blood is drawn into the syringe and that the tablet binder and pH controlling substance require added cost and additional manufacturing complexities. Thiel then discloses a new process for producing a web of heparin that may be placed directly into the hub of a needle through which blood to be analyzed is drawn. Thus, although Thiel recognizes problems associated with the manufacturing of a tablet, Thiel does not address a solution whereby existing manufacturing processes and apparatus can be used, nor does Thiel address the special problem associated with producing pledgets with low unit dosages of heparin.

U.S. Pat. No. 4,371,516 by Gregory et al., issued Feb. 1, 1983, discloses articles for carrying chemicals, particulary pharmaceutical dosages, which dissolve rapidly in water. The articles include a carrier material such as hydrolysed gelatin, dextran, dextrin, or alginates. Gregory et al., also disclose a process for preparing the articles by subliming solvent from a composition comprising the pharmaceutical in a solution of the carrier material in a solvent. The carrier bodies disclosed by Gregory et al., are rather large, about 0.75 ml in volume, and comprise a high concentration of pharmaceutical. It would be beneficial to produce a carrier body more amenable to use in a small syringe, such as a one cubic centimeter syringe. However, smaller bodies are much more likely to stick in the container in which they are produced. Gregory et al. attempts to address this problem in the larger tablets by using a surfactant.

Gregory et al. also disclose that the solution to be sublimed has a solids concentration of about 73 mg/ml or higher. Solutions with these high solids concentrations give rise to tablets that are very difficult to redissolve in solvents such as blood, particularly when rapid mixing is desired.

Pledgets for anticoagulating blood samples should preferably contain a relatively low concentration of heparin to be useful when it will be desirable to measure free ions in the blood, particularly calcium ions. However, the manufacture of extremely small pledgets of heparin is difficult to implement. The small size makes it difficult to remove the pledget from its mold without inflicting damage to the pledget. And at very small sizes, forces such as static electricity become significant and further complicate handling.

It is therefore desirable to increase the size of the pledget without significantly increasing the heparin activity content. It has been suggested that filtering paper or mineral fibers may be used as a carrier body, however, these may interfere with the proper operation of the blood sampling device, since these materials do not dissolve and it is difficult to accurately control the unit dosage.

The use of materials such as hydrolysed gelatin or polysaccharrides such as dextran, dextrin and alginates as pharmaceutical carrier bodies for large tablets (i.e. 0.5 ml and larger) has also been described. However, these tablets are too large to use in standard blood sampling devices, which require pledget sizes less than about 0.075 ml.

The production of smaller pledgets, i.e. less than about 0.075 ml, presents special problems. The above-mentioned carrier body materials tend to stick to mold walls during formation of the pledget, and hence, small pledgets are often damaged by attempts to remove them from the mold. Irregularities, such as nicks, burrs, or foreign matter on the mold wall compound this problem by making the smaller pledget more difficult to remove. It would also be highly desirable to eliminate the problems of the pledget sticking in the mold without resorting to additional chemicals, such as surfactants.

The production of such a pledget, for example by lyophilization, also requires that particular problems be addressed. The solution from which the pledget is derived must contain a sufficient amount of filler to retain adequate strength in the pledget, while being low enough in density to permit rapid dissolution in the blood sample. It would also be highly desirable to eliminate the problems of the pledget sticking in the mold without resorting to additional chemicals, such as surfactants.

SUMMARY OF THE INVENTION

According to the present invention, an anticoagulating pledget comprises a heparin salt and a glucose polymer filler. The pledget is useful for anticoagulating a blood sample, and in one embodiment is capable of providing from about 2 to about 15 U.S.P. units of anticoagulating activity per milliliter of a blood sample.

In one embodiment of the present invention, the glucose polymer filler includes the material dextran. The dextran preferably has a molecular weight from about 20,000 to about 500,000, more preferably from about 60,000 to about 90,000, to minimize the sticking of the pledget to the mold that it is formed in.

The pledget preferably has a density from about 20 mg/ml to about 30 mg/ml, more preferably from about 25 mg/ml to about 30 mg/ml and preferably carries less than about 15, more preferably from about 2.0 to about 7.8, most preferably from about 2.8 to about 7.0 U.S.P. units of heparin activity.

Heparin useful in the pledget of the present invention can be any heparin salt, including ammonium heparin, sodium heparin, lithium heparin, magnesium heparin, calcium heparin, or mixtures thereof. In one embodiment according to the present invention, the anticoagulant is lithium heparin.

According to the present invention, the heparin has an activity concentration from about 140 units/mg to about 250 units/mg, more preferably from about 160 units/mg to about 190 units/mg. In another embodiment of the present invention, its preferable to use a heparin compound having a very high activity concentration, such as greater than about 190 units/mg. It is believed that the use of heparin with such high activity concentrations will assist in minimizing any free ion bias in the blood measurement, as discussed in more detail hereinbelow.

The present invention further provides a process for producing the heparin pledget composition. The process is a lyophilization process and includes the steps of forming a solution comprising a soluble filler and an anticoagulant, and freeze drying the solution in a mold to form a pledget. The mold is preferably made of highly polished, anodized aluminum and is preferably thoroughly cleaned between each use. More preferably, the mold is cleaned with deionized or distilled water and a stiff brush between each lyophilization cycle.

The solution to be lyophilized preferably contains a dissolved solids content from about 20 mg/ml to about 30 mg/ml so that the lyophilized pledget has the preferred density, and the solution is more easily lyophilized.

The anticoagulant pledget of the present invention does not substantially bias free ion measurements, particularly free ionized calcium measurements, and the use of a filler allows existing manufacturing equipment to be utilized and the pledget can be produced and handled at a minimum expense.

According to one preferred embodiment of the present invention, the syringe has a recommended draw volume of about 3 cubic centimeters and the pledget contains from about 5.5 to about 7.8 U.S.P. units of heparin activity. In another preferred embodiment, the syringe has a recommended draw volume of about 1 cubic centimeter and the pledget contains from about 2.0 to about 3.2 U.S.P. units of heparin activity.

The present invention also provides a method for measuring free ion concentrations in a blood sample by collecting the blood sample into a receptacle such that a pledget in the receptacle provides less than about 15 U.S.P. units of heparin activity per milliliter of blood collected.

The composition of the pledget according to the present invention and the process used to produce the pledget according to the present invention, alleviate the problems inherent in the prior art. The use of a glucose polymer filler, particularly dextran, having a molecular weight from about 60,000 to about 90,000, yields a pledget having a desirable volume and U.S.P. activity concentration of heparin, while minimizing the problems associated with mold sticking without the use of a surfactant. The pledget has a sufficient strength and density to be handled and can be manufactured economically.

The process for producing the pledget also eliminates the problems associated with mold sticking by providing polished anodized aluminum molds and a process for thoroughly cleaning the molds between uses.

DETAILED DESCRIPTION OF THE PREFERRED EMBODIMENTS

A process for the lyophilization of biologicals having a predetermined unit dosage is disclosed in commonly-owned U.S. Pat. No. 4,521,975, by Bailey, incorporated herein by reference in its entirety. The process described by Bailey is directed to lyophilizing solutions with large concentrations of heparin, thereby forming pledgets having from about 100 to about 200 U.S.P. units of heparin activity. The use of such high dosages of anticoagulant activity is common in the art.

To prevent the bias of free ion measurements, for example, free calcium ion measurements, it is preferable to use a low concentration of heparin as an anticoagulant. Accordingly, it is preferable to use a heparin activity concentration of less than about 20 units/ml of blood, more preferably from about 2 units/ml of blood to about 15 units/ml of blood, and most preferably from about 2.3 units/ml to about 2.8 units/ml of blood. The preferred concentrations result from balancing the opposing objectives of employing an effective amount of heparin to prevent coagulation of the blood, while minimizing chelation of the free ions. This range of heparin concentration is sufficient to prevent clot formation for at least about 75 minutes if the sample is kept on ice, and for up to about 30 minutes at room temperature. Preferably, the blood sample is put on ice immediately after collection.

The concentration of heparin in the heparin pledget should be selected to yield the preferred heparin concentrations in the blood sample. For example, when using a three cubic centimeter (3 cm$^3$) syringe, with a recommended draw volume of 0.5 to 2.8 cubic centimeters, approximately 7.0 U.S.P. units of heparin are preferably carried in the pledget. If a one cubic centimeter (1 cm$^3$) syringe is utilized, with a recommended blood draw volume of 0.2 to 1.0 cubic centimeters, approximately 2.8 U.S.P. units of heparin are preferably carried in the pledget. This level of heparin is even lower than the safety factor discussed by Bailey in U.S. Pat. No. 4,521,975, at Column 5, lines 46–48. That is, Bailey discloses that it is desirable to add an additional 10 units of heparin activity to each pledget to insure that the unit dosage will be sufficient. The pledgets produced according to the present invention must be produced with much tighter control.

Heparin salts are typically in the form of heparin having any monovalent or divalent cation attached to the heparin. Examples of heparin salts that can be utilized in the present invention include, but are not limited to, lithium heparin, ammonium heparin, sodium heparin, magnesium heparin, and calcium heparin. In one preferred embodiment of the present invention, lithium heparin is utilized. Lithium heparin is particularly advantageous because it does not bias most blood measurements to any significant degree.

Commercially available heparin can be obtained with various activities. For example, 1 milligram of low activity concentration heparin may be capable of providing 140 U.S.P. units (140 units/mg) of anticoagulation activity, while a milligram of high activity concentration heparin may provide 250 U.S.P. units (250 units/mg) of activity. According to the present invention, heparin having an activity concentration from about 140 units/mg to about 250 units/mg, more preferably from about 160 units/mg to about 190 units/mg, is utilized.

While not wishing to be bound by any theory, the present inventors believe that the chelation of free ions, such as calcium ions, is related to the number of sulfate groups on the heparin molecule. However, the number of sulfate groups remains constant as the activity concentration of the heparin increases. Thus, the chelating effect of the heparin is not believed to be due to the activity of the heparin, but only due to the total number of sulfate groups present, which depends on the total number of heparin molecules present. Therefore, it would be advantageous to use heparin having the highest activity available. For example, heparin having a activity concentration of greater than about 190 units/mg can be used so that the quantity of heparin, and the number of sulfate groups, in the blood sample is minimized. However, this aggravates the problems associated with producing a pledget having very low amounts of heparin for dissolution in a blood sample of one or three cubic centimeters.

Thus, in accordance with the present invention, the amount of heparin contained in a unit dosage will be very small. If the pledget was made purely of heparin and the heparin had an average activity of about 180 units/mg of heparin, the heparin would have a mass of approximately 16 micrograms to provide 2.8 U.S.P. units of heparin per pledget. Such a small size would be extremely difficult to handle and process. According to the present invention, the size of the pledget is increased by adding a filler material. Preferably, the filler material includes a glucose polymer, more preferably the filler material comprises the glucose polymer dextran.

Polymers such as dextran are available in a number of grades, for example, clinical or industrial grade. According to the present invention, it is preferable to use a clinical grade dextran having a high purity, such as that available from the Sigma Chemical Company, St. Louis, Mo. Clinical grade dextran also has a finer and more consistent crystalline size than industrial grade. It has been found that clinical grade dextran facilitates easy mold release, as will be discussed in more detail hereinbelow.

Dextran is available in a wide range of molecular weights, and many factors determine the proper molecular weight to use. After extensive testing, it was found that the preferable range of molecular weight for dextran is between about 20,000 and about 500,000, more preferably between about 60,000 and about 90,000.

The selection of dextran as the preferred glucose polymer filler, and particularly dextran having the preferred molecular weights, is the result of balancing many factors relating to the properties of the pledget and the factors involved in producing the pledget. The molecular weight of the glucose polymer filler must be high enough such that the structural integrity, i.e. strength, of the pledget is maintained. Since the pledget produced by the process of the present invention is still relatively small, on the order of 0.010 to 0.035 milliliters in volume, it is desirable that the pledget have a high degree of mechanical strength so that there is a high probability of surviving the stresses and pressure placed on the pledget during manufacturing and handling.

It is also desirable to control the density of the heparin containing pledget. Accordingly, it has been found that a pledget having a density of less than about 20 mg/ml will have a tendency to fall apart under the stresses normally incurred during handling and manufacturing. Likewise, a pledget density greater than about 30 mg/ml is typically too dense to effectively dissolve in the blood sample. Accordingly, it is preferable that the pledget density be between about 20 mg/ml and about 30 mg/ml and more preferably between about 25 mg/ml and about 30 mg/ml.

The glucose polymer may be utilized as 100 percent of the filler composition, or may be mixed with materials such as mannitol. Mannitol is a straight-chain hexahydric alcohol, having the nominal composition $C_6H_8(OH)_6$. Preferably, the glucose polymer comprises 100 percent of the filler composition. It has been found that mannitol does not provide the strength necessary to form an adequate pledget when used as the only filler.

According to the present invention, it is preferable to form the pledget composition by a lyophilizing process.

However, one of the problems encountered producing pledgets with a filler by a lyophilizing process is that glucose polymers such as dextran have a tendency to stick to the molds used to form the pledgets.

To prevent the sticking of the pledget in the mold, it is preferable to use highly polished anodized aluminum molds during the lyophilization process. Preferably, the molds are thoroughly cleaned after each use by soaking the mold in warm deionized, or distilled, water for about 2 minutes and then cleansing the mold with a stiff brush. A process useful for producing a pledget according to the present invention will be described with reference to the Figures. The process will be described as pertaining to a pledget comprising heparin and dextran, but is not limited thereto.

Figure 1:
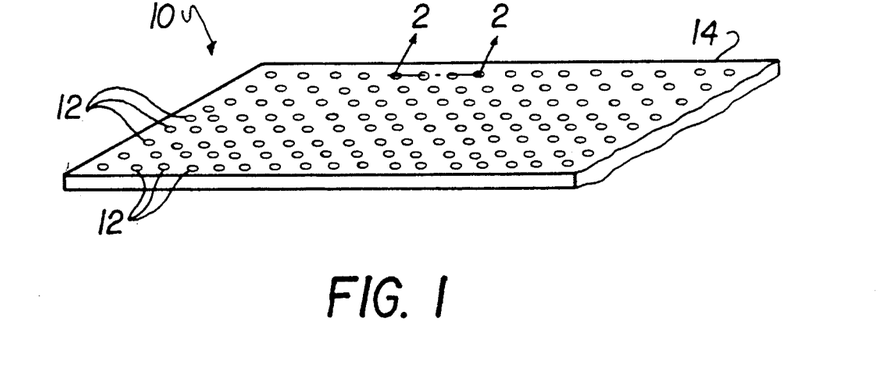
FIG. 1 is a perspective view of a tray of the present invention adapted for use in a lyophilization process.
Figure 2:
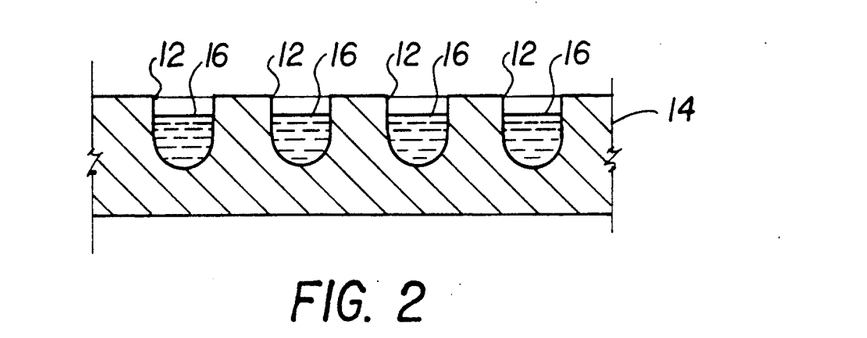
FIG. 2 is a fragmentary enlarged sectional view taken in a plane of line 2—2 of FIG. 1.

A tray 10 having rows and columns of wells 12 formed in a top surface thereof used in a lyophilization process for primarily biological drugs and other pharmaceuticals is shown in FIGS. 1 and 2. The wells, or molds, 12 are drilled or formed in an upper surface 14 of the tray, and the wells are of a predetermined volume. The wells 12 are adapted to be filled with a solution 16 having a predetermined concentration of the heparin and the filler to be lyophilized, or freeze dried. The wells 12 correspond to a single unit dosage, when filler is accounted for, of the heparin that is lyophilized.

The tray 10 of wells 12 containing the solution 16 is placed in a commercially available freeze dryer 18 (FIG. 6), where the solution 16 undergoes a lyophilization process, to be described in more detail hereinafter. Generally, the water content of the solution 16, in the form of an ice matrix formed by freezing the solution, is selectively removed by sublimation, drying and heating under vacuum conditions, during the lyophilization process. The product of the process is a dry, solid pledget 20 (FIG. 5), having no significant water content and is therefore capable of being stored for extended periods of time.

The tray 10 (FIGS. 1 and 2) is made of a thermally conducting material, for example, aluminum. The aluminum is preferably anodized to prevent corrosion and the wells 12 are highly polished to facilitate removal of the pledgets. The presence of small nicks or burrs in the mold will hamper the removal of the pledget due to the small pledget size. After removal of the pledgets, the wells 12 are thoroughly cleaned, for example, by soaking in warm deionized water and then brushing before the next use. If the molds are not thoroughly cleaned after each use, the pledget will have a tendency to stick to the mold. Further, irregularities on the mold walls may cause air bubbles to form, which may deleteriously affect the volumetric control that is important to the present invention.

The tray is of rectangular solid configuration of relatively narrow thickness. The wells 12 are of dome-like shape and are formed in the upper surface 14 in rows and columns over the face of the tray 10.

The tray 10 is particularly suited to conducting the cold temperatures, around minus 40° C., encountered in the freeze dryer 18 (FIG. 6), necessary to the lyophilization process. The wells 12 of the tray 10 are spaced in rows and columns over the entire top surface of the upper surface 14. The wells 12 in a preferred embodiment number 2064 per tray, but the tray 10 may contain any number of wells 12. The trays are preferably sized so that several trays are placed on a single thermally controlled shelf 30 (FIG. 3), a plurality of which shelves are mounted in a superimposed relationship within the freeze dryer 18 (FIG. 6). It can therefore be seen that several thousand individual pledgets 20 (FIG. 5) are made in a single lyophilization cycle.

The wells 12 of the tray 10 are formed into the upper surface 14 in such a manner as to have a set or predetermined volume. The volume corresponds to a set number of U.S.P. units of heparin, when the solution 16 to fill the predetermined volume is at a set concentration of heparin dissolved in the solvent, which is preferably sterile water. According to the present invention, from about 2 to about 15 U.S.P. units of heparin activity are preferably contained in a single dosage pledget, more preferably from about 2.8 to about 7.0 U.S.P. units.

The wells 12 are configured in an inverted dome shape (FIG. 2). For a unit dosage, the wells 12 preferably have downwardly and inwardly sloping sides, terminating in a dome shape. In one embodiment, the wells have a volume of about 35 microliters. The wells 12 are small enough in diameter, or bore, to be filled, when immersed in the solution 16 by capillary action. The dome shape and inward sloping sides facilitate removal of the pledgets after freeze drying.

Figure 3:
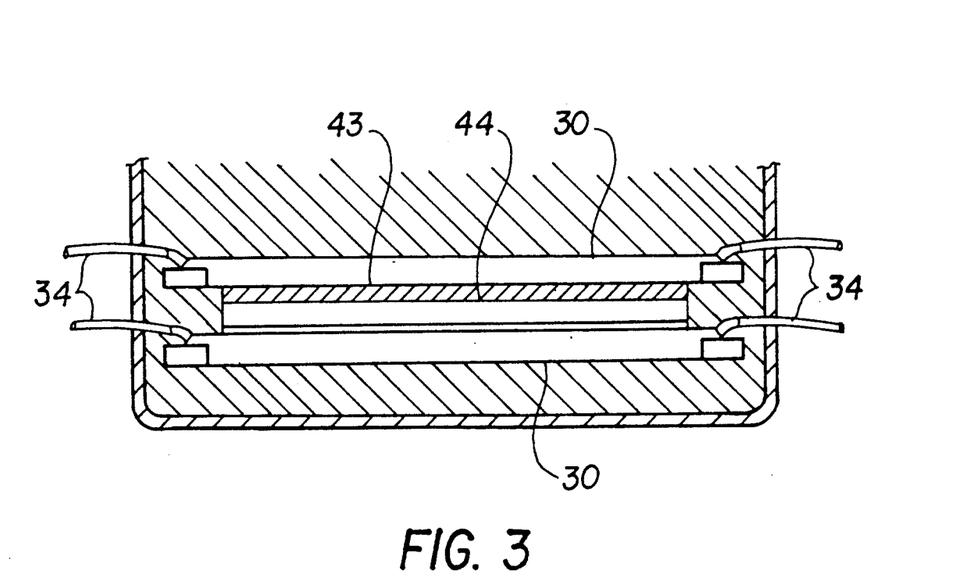
FIG. 3 is a fragmentary schematic sectional view of a freeze dryer, a pair of superimposed heating shelves, intermediate insulation and the tray shown in FIG. 1 shown in full.

The tray 10, made of a thermally conducting material, assists in initial heat transfer to freeze the solution 16 contained in the wells 12, and then later assists in the application of heat the solution 16 for sublimation. It has been found that, during the freezing step of lyophilization, it is desirable to freeze the solution 16 from the bottom to the top of the well 12. The thermal gradient is preferably applied very quickly so that the solution is supercooled. In this way, the nucleation of the material will dominate the crystal growth. This will lead to a very fine grain structure giving enhanced solubility characteristics. A temperature gradient wherein the solution 16 at the bottom of the well is cooler than the solution at the top of the well 12 is maintained by insulating the upper surface 14 from the next upper shelf 30 (FIG. 3). An insulator 43, such as Styrofoam ™, with an intermediate plexiglass sheet 44, is placed over the tray 10. The insulator 43 is preferably wrapped in aluminum foil to augment its insulation properties. The insulator 43 maintains the temperature gradient desired, slightly warmer at the top of the well 12 than at the bottom, while the plexiglass sheet 44 prevents Styrofoam ™ or any other contaminant from entering the solution 16 in the wells 12.

An appropriate freeze dryer 18 (FIG. 6) is required, such as the model 25 S.R.C. built by The Virtis Company, Inc., of Gardiner, N.Y. The freeze dryer 18 typically includes a drying chamber 32 containing trays 10 (FIG. 1) and product solution 16 to be lyophilized. The trays are supported on the several superimposed thermally controlled shelves 30. The shelves 30 have passageways (not shown) which are connected to conduits 34 through which liquid cooling and heating medium flows (FIG. 3). The liquid or fluid medium is pumped by a centrifugal pump 35 through the conduit 34, the shelves 30, a fluid cooler 36 and a fluid heater 38. Depending on the particular step in the lyophilization process, the cooler 36 or the heater 38 would be activated.

Figures 7, 8:
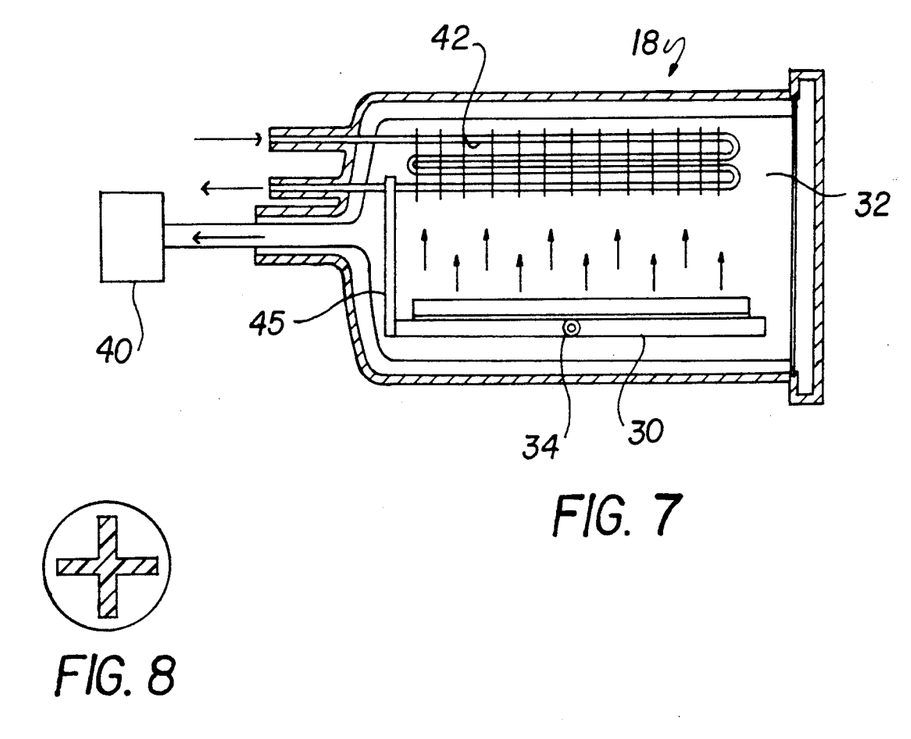
FIG. 7 is a diagrammatic vertical section view of a drying chamber of a freeze dryer utilizing the tray shown in FIG. 1.
FIG. 8 is an enlarged sectional view taken in the plane of line 8—8 of FIG. 5.

The drying chamber 32 is adapted to be evacuated by a vacuum pump 40 (FIG. 7). A tube-type condenser 42 is superimposed above the shelves 30 and within the drying chamber 32. During the sublimation portion of the lyophilizing process the shelves 30 are heated and the drying chamber is evacuated, and the vapor driven from the wells 12 condenses as ice on the condenser. A baffle plate 45 prevents the vapors from being drawn directly out of the drying chamber 32 by the vacuum pump 40.

The dry heparin containing pledget 20 (FIG. 5) is removed after lyophilization by turning the tray 10 (FIG. 1) upside down or by application of a relatively small air pressure supplied by a blower (not shown). The heparin pledget 20 has a predetermined U.S.P. unit dosage of heparin dependent upon both the initial concentration of heparin and filler in the solution 16 and the volume of the wells 12 occupied by the solution.

To successfully manufacture a pledget 20 (FIG. 5) of heparin having a preset U.S.P. unit value, it is important that the solution 16 contains a proper concentration corresponding to the volume of the wells 12. For a given well 12 having a set volume, the solution concentration can be varied in order to obtain different U.S.P. unit values. Alternatively, for a given concentration of solution 16, the volume of the wells 12 can be varied in order to obtain the desired final unit dosage of the pledget 20.

It is first necessary, in the method of preparation of the solution 16, that a batch volume be determined. In describing the method or process of preparing the solution, a 2500 milliliter batch will be utilized to prepare pledgets 20 having 7.0 U.S.P. units of heparin activity each. Variations in the procedure will be adaptable to alter unit dosages, either by varying the volume of the wells 12 or the concentration of solution 16, or both.

If the solution 16 is to have a volume of 2500 milliliters, then the number of pledgets being made can be calculated by dividing the total volume of the batch, 2500 milliliters, by the volume of the wells, 35 microliters. This results in a finding that about 71,430 pledgets can be made from a 2500 milliliter initial batch.

The total U.S.P. units of heparin activity required can then be calculated by multiplying the total number of pledgets by the U.S.P. unit dosage desired per pledget. This results in multiplication of 71,430 pledgets times 7.0 U.S.P. units per pledget, equaling about 500,000 U.S.P. units.

The mass of a unit of heparin activity can typically be obtained from the label of the heparin container, the heparin being in a dry powder form. For example, a given lot may contain an average of 176 U.S.P. units of anticoagulation activity per milligram of heparin, which when divided into the total units desired in the solution, gives the weight of the heparin in grams necessary for the proper solution, in this case about 2841 milligrams. The dry heparin is weighed out and dissolved in 2500 milliliters of sterile water and a solution 16 compatible with a well volume of 35 microliters results.

Since the solution 16 as described above would yield a heparin pledget composed of pure heparin with a very small volume and/or a very weak structure, a water soluble filler is added to the solution, to yield a pledget having a larger and more easily handled volume. The filler preferably comprises a glucose polymer, more preferably the glucose polymer dextran, as described hereinabove.

According to the present invention, it is preferable to attain a concentration of between about 20 and about 30, more preferably between about 25 and about 30 milligrams of dissolved material per milliliter of solution. When using a filler, it has been found that a concentration below about 20 mg/ml will yield a pledget too weak to be easily handled. Above about 30 mg/ml, the pledget formed is too dense to efficiently solubilize in the blood sample.

To attain a solids concentration of about 25 mg/ml, and hence, a pledget having a density of about 25 mg/ml, about 60 grams of dextran are added to the 2500 milliliter solution, yielding a total concentration of about 25 mg/ml of solids dissolved in the solution. Upon lyophilization of the pledget, each pledget would occupy a volume approximately equal to the well volume, 35 microliters. A pledget with such a volume and density is more easily handled and the cost of manufacture is significantly reduced when compared to a pledget made purely of heparin.

Figure 4:
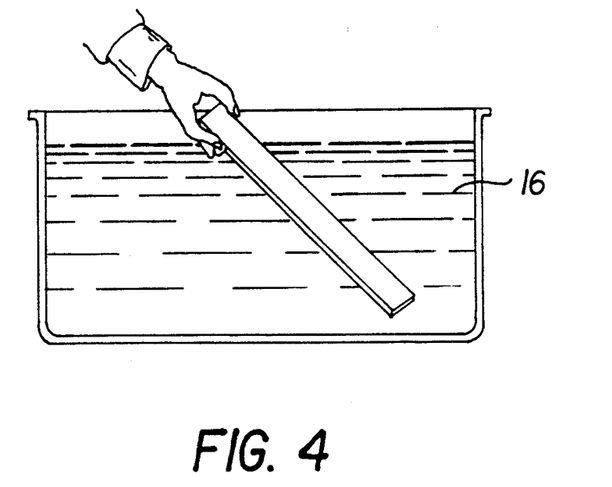
FIG. 4 is an elevational view showing a method for filling wells of the tray shown in FIG. 1 with a biological solution.

The solution 16 is then transferred to the well 12, by an automatic pipette, not shown, or as shown in FIG. 4, by immersion of the tray 10 into the solution 16, which then fills the wells 12, in part by capillary action.

The lyophilization process parameters are important to the success of creating a freeze dried pledget 20 of heparin. Four basic conditions are important for freeze drying. First, the product must be solidly frozen below its eutectic point. Then, a condensing surface having a temperature less than minus 40° C. is needed. The system should then be able to evacuate to an absolute pressure of, for example, between about 5 and about 25 millitorr (0.667 to about 3.33 Pa). Finally, the system must have a heat source, controllable to temperatures between minus 40° C. and 65° C. The heat source supplies the heat of sublimation necessary to drive water vapor directly from the solid frozen ice.

During the freezing portion of the lyophilization process, the superimposed shelves 30 (FIGS. 3 and 6) receive refrigerated fluid through the conduits 34. The trays 10 are in turn supported on the freeze dryer shelves 30. Therefore, the conducting material 28 assists in rapidly and economically freezing the solution 16 below the solution eutectic point, which is necessary for complete freeze drying without danger of some moisture remaining in the matrix of the pledget 20. Remaining moisture can result in a condition known as "meltback", in which some water is returned to the pledget 20.

The cooler 36 is activated and the solution 16 is frozen in the wells 12. The proper freezing point is determined by matching the solution temperature to the shelf temperature and by visually observing that peaks are formed in the ice formed in the wells 12, the peaks indicating that the proper temperature gradient was maintained.

Once the freezing portion of the lyophilization process is complete, the frozen product is subjected to the heat of sublimation under evacuated conditions. This is the drying portion of the lyophilization process. The insulator 43 and plexiglass sheet 44 are removed to allow absolute pressure levels to be reached quickly and to avoid loss of air pockets in the insulator, if Styrofoam TM is used as the insulator 43.

The condenser 42 and vacuum pump 40 are activated at approximately the same time during the drying cycle. the condenser 42 is allowed to reach minus 40° C., while the vacuum in the drying chamber 32 should reach one hundred millitorr (13.3 Pa) or less, at which pressure the thermally controlled shelves 30 are heated by activating the heater 38.

The frozen solution is preferably dried for from about three to about seven hours, more preferably about four hours. The thermally controlled shelves 30 should, through the remainder of the lyophilization process drying cycle, be at about 30° C., while the condenser 42 is in the range of about minus 48° C. to about minus 60°

C. and the vacuum is maintained at between about 50 and about 150 millitorr (6.67 to about 20 Pa).

Once the drying cycle is completed, the vacuum is slowly released. Rapid release can cause the pledgets 20 to be blown out of the wells 12.

Figure 5:
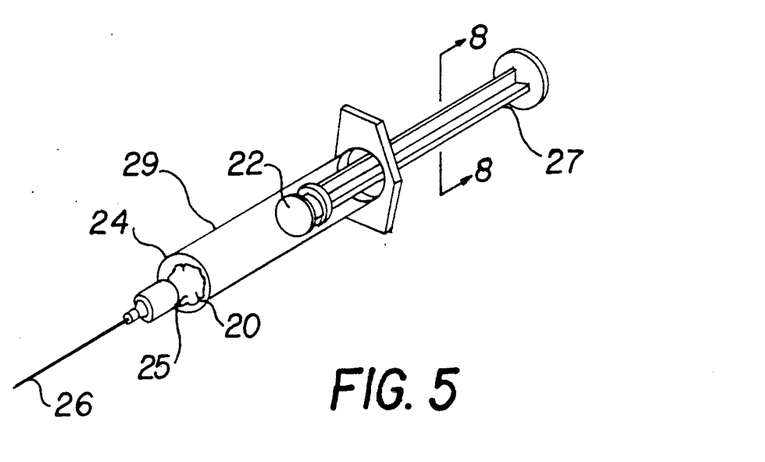
FIG. 5 is a perspective view of a syringe containing a dried pledget produced by the tray shown in FIG. 1.
Figure 6:
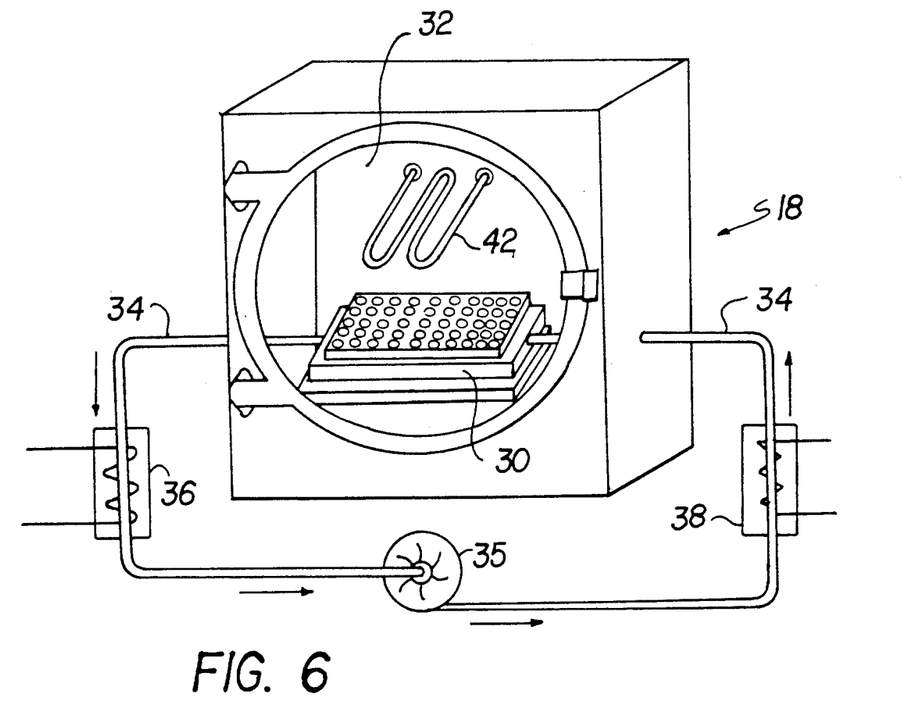
FIG. 6 is a diagrammatic view of a freeze dryer and associated system utilizing the tray shown in FIG. 1.

Once lyophilized, the pledget 20 can be stored in a syringe 22 (FIG. 5). The pledget 20 is ready for immediate use in conjunction with the aspiration of a blood sample. The pledget 20 is placed inside a barrel 24 of the syringe 22, near an end member 25 of the barrel, to which end member is mounted an hypodermic needle 26. A plunger 27 preferably of X-shaped cross section (FIG. 8) having a double-lipped sealing member 29 rotatably mounted at one end thereof is inserted along the barrel 24, placing the pledget 20 between the end member and sealing member.

The syringe 22, without a needle 26, but including the plunger 27 and sealing member 29, as well as the enclosed pledget 20, is placed in a sterile plastic envelope (not shown) and stored until such time as a patient's blood sample is needed. When the syringe is needed, the envelope is opened, the hypodermic needle 26 is attached, and the blood sample then aspirated from a blood-carrying vessel of the patient. It will be understood that once the pledget 20 contacts the blood, the pledget dissolves into solution, treating the blood at that time with anticoagulant properties and therefore allowing the blood to be analyzed for gas or free ions, without interference from clotting. The filler dissolves and does not significantly bias subsequent measurements.

EXAMPLES

Tests were performed to determine if resultant electrolyte readings are accurate when blood samples are heparinized according to the present invention.

In the first test, blood samples heparinized according to the present invention were compared to blood samples that were anticoagulated according to the prior art. In this instance, blood samples heparinized according to the present invention were compared to blood samples heparinized according to U.S. Pat. No. 4,687,000 by Eisenhardt, issued on Aug. 18, 1987. The results are summarized in Table 1 below.

TABLE 1

| Average $Ca^{++}$ measurement (millimoles) | | | | | |
|---|---|---|---|---|---|
| | Patient No. | | | | |
| | 1 | 2 | 3 | 4 | 5 |
| Sample 1 | 1.21 | 1.26 | 1.27 | 1.22 | 1.20 |
| Sample 2 | 1.21 | 1.24 | 1.28 | 1.25 | 1.23 |
| Sample 3 | 1.24 | 1.27 | 1.31 | 1.28 | 1.24 |
| | Patient No. | | | | |
| | 6 | 7 | 8 | 9 | 10 |
| Sample 1 | 1.20 | 1.34 | 1.23 | 1.24 | 1.21 |
| Sample 2 | 1.21 | 1.30 | 1.25 | 1.21 | 1.27 |
| Sample 3 | 1.25 | 1.31 | 1.29 | 1.25 | 1.26 |

Sample 1 represents blood samples heparinized according to the present invention, using a 1 cubic centimeter syringe having 2.8 U.S.P. units of dry lithium heparin contained therein. Sample 2 represents blood samples heparinized according to the present invention, using a 3 cubic centimeter syringe having a 7.0 U.S.P. units of dry lithium heparin contained therein. Sample 3 represents blood samples heparinized according to the process described by Eisenhardt. For this analysis, blood was drawn from ten healthy volunteers between 21 and 55 years of age into test syringes, which were placed on ice until analysis. Blood samples were measured for free ionized calcium. As the results in Table 1' show, values for each volunteer are essentially identical for both anticoagulating techniques.

To determine the effect of the pledget compositions of the present invention on the free ionized calcium measurements, another test was run to compare the values of the heparinized blood samples to those of a reference, unheparinized sample. The results are summarized in Table 2 below.

TABLE 2

| Average $Ca^{++}$ measurement (millimoles) | | | | | | |
|---|---|---|---|---|---|---|
| | Patient No. | | | | | |
| | 1 | 2 | 3 | 4 | 5 | 6 |
| Sample 4 | 1.24 | 1.28 | 1.26 | 1.26 | 1.21 | 1.24 |
| Sample 5 | 1.22 | 1.27 | 1.27 | 1.26 | 1.20 | 1.24 |
| Sample 6 | 1.25 | 1.33 | 1.27 | 1.25 | 1.21 | — |

Blood samples were drawn into syringes heparinized according to the present invention. Sample 4 represents blood samples drawn into a 1 cubic centimeter syringe containing 2.8 U.S.P. units of lithium heparin activity therein, and Sample 5 represents blood drawn into 3 cubic centimeter syringes having 7.0 U.S.P. units of lithium heparin therein. Sample 6 represents a control group, that is, blood samples which were not heparinized. Blood was drawn from each of six healthy volunteers between the ages of 21 and 55 years of age. Since elevated heparin concentrations are detrimental to free ionized calcium, this was the electrolyte measured. As illustrated in Table 2 above, the values for the heparinized and unheparinized samples are virtually identical. Further, none of the blood samples collected according to the present invention clotted over a period of 75 minutes.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. A method for substantially preventing the coagulation of blood in a syringe for at least a predetermined time period while reducing inaccuracies in the determination of the free calcium ion concentration of the blood, comprising:

providing a predetermined amount of a heparin salt which will substantially prevent coagulation of blood;

providing a predetermined amount of a water-soluble filler material;

combining said heparin salt and said filler material;

making a plurality of pledgets consisting essentially of said heparin salt and said filler material, each of said pledgets having an amount of filler material sufficient to allow for process and handling of said pledget to properly place it in a syringe;

placing one of the pledgets in a syringe;

obtaining a blood sample in said syringe such that the concentration of heparin in the blood sample is less than about 20 U.S.P. units per milliliter of blood;

inputting at least portions of said blood sample from said syringe into a testing apparatus for analyzing said blood sample portions; and determining the free calcium ion concentration associated with said blood sample portions in the absence of a free ion compensating additive while reducing error in said determination due to use of said heparin giving said heparin concentration.

2. A method as claimed in claim 1, wherein said step of making pledgets includes:
providing a tray having a number of wells;
placing combined heparin and filler material in each of said wells;
lyophilizing said combined heparin and filler material while in said wells;
removing said pledgets from each of said wells after said lyophilizing.

3. A method as claimed in claim further including:
maintaining said syringe free of any material that would influence the determination of said free calcium ion concentration.

4. A method as claimed in claim 1, wherein said concentration of heparin in the blood sample is from about .2 to about 15 U.S.P. units per milliliter of blood.

5. A method for measuring the free ion concentration in a blood sample, comprising the steps of:
a) collecting a blood sample into a receptacle containing a heparin-containing pledget, said heparin being in an amount to substantially prevent the biasing of free ion measurements; and
b) measuring the free ion concentrations in the blood sample in the absence of a free ion compensating additive;
wherein said pledge is constructed so as to provide less than about 15 U.S.P. units of heparin activity per milliliter of blood collected and said pledget comprises a glucose polymer filler.

6. A method as recited in claim 5, wherein said measuring step includes measuring for free ionized calcium.

7. A method as recited in claim 5, wherein said glucose polymer filler consists essentially of dextran.

8. A method as recited in claim 5, wherein said pledget is constructed so as to provide between about 2.3 and about 2.8 U.S.P. units of heparin activity per milliliter of blood collected.

* * * * *